United States Patent
Melrose et al.

(10) Patent No.: US 11,045,491 B2
(45) Date of Patent: Jun. 29, 2021

(54) ANTI-VIRUS AGENT AND METHOD FOR TREATMENT OF VIRAL INFECTION

(71) Applicant: RECCE PHARMACEUTICALS LTD, Bentley (AU)

(72) Inventors: Graham John Hamilton Melrose, Mount Claremont (AU); Michele Keryn Dilizia, Hillarys (AU)

(73) Assignee: RECCE PHARMACEUTICALS LTD, Western Australia (AU)

(*) Notice: Subject to any disclaimer, the term of this patent is extended or adjusted under 35 U.S.C. 154(b) by 31 days.

(21) Appl. No.: 15/771,858

(22) PCT Filed: Feb. 17, 2017

(86) PCT No.: PCT/AU2017/050139
§ 371 (c)(1),
(2) Date: Apr. 27, 2018

(87) PCT Pub. No.: WO2017/139849
PCT Pub. Date: Aug. 24, 2017

(65) Prior Publication Data
US 2018/0338994 A1    Nov. 29, 2018

(30) Foreign Application Priority Data

Feb. 19, 2016 (AU) .............................. 2016900595
Jul. 11, 2016 (AU) .............................. 2016902715

(51) Int. Cl.
*A61K 9/00* (2006.01)
*A61K 31/78* (2006.01)
(Continued)

(52) U.S. Cl.
CPC ............ *A61K 31/78* (2013.01); *A61K 9/0019* (2013.01); *A61K 9/0053* (2013.01);
(Continued)

(58) Field of Classification Search
CPC ...................................................... A61K 31/78
See application file for complete search history.

(56) References Cited

U.S. PATENT DOCUMENTS

| | | |
|---|---|---|
| 5,290,894 A | 3/1994 | Melrose et al. |
| 6,060,235 A | 5/2000 | Neenan et al. |
| | (Continued) | |

FOREIGN PATENT DOCUMENTS

| | | |
|---|---|---|
| AU | 2010100972 A4 | 10/2010 |
| CA | 2198158 C | 9/2001 |
| | (Continued) | |

OTHER PUBLICATIONS

International Preliminary Report on Patentability for corresponding application PCT/AU2017/050139 dated Mar. 23, 2017.
International Search Report for corresponding application PCT/AU2017/050139 dated Apr. 10, 2017.
Feng et al., Abstract for "Acrolein is a major cigarette-related lung cancer agent: Preferential binding at p53 mutational hotspots and inhibition of DNA repair", PubMed—NCBI, Proc. Natl. Acad. Sco. U.S.A., Oct. 2006.
(Continued)

*Primary Examiner* — Paul W Dickinson
(74) *Attorney, Agent, or Firm* — Norris McLaughlin, PA

(57) ABSTRACT

A method of treatment of viral infection in a subject comprising administering to the subject a copolymer comprising an acrolein derived segment or a polyacrolein oligomer segment and a polyalkylene glycol oligomer segment, the copolymer having a molecular weight of no more than 1500 Daltons.

13 Claims, 2 Drawing Sheets

(51) Int. Cl.
*A61K 47/10* (2017.01)
*A61P 31/22* (2006.01)
*A61P 31/18* (2006.01)
*A61P 31/16* (2006.01)
*A61K 9/20* (2006.01)
*A61K 9/48* (2006.01)

(52) U.S. Cl.
CPC .............. *A61K 9/0073* (2013.01); *A61K 9/20* (2013.01); *A61K 9/48* (2013.01); *A61K 47/10* (2013.01); *A61P 31/16* (2018.01); *A61P 31/18* (2018.01); *A61P 31/22* (2018.01)

(56) References Cited

U.S. PATENT DOCUMENTS

| | | | |
|---|---|---|---|
| 6,060,571 | A | 5/2000 | Werle et al. |
| 6,723,336 | B1 | 4/2004 | Melrose |
| 7,629,002 | B2 | 12/2009 | Melrose et al. |
| 9,119,394 | B2 | 9/2015 | Melrose |
| 2019/0202908 | A1* | 7/2019 | Zhao ................ C07K 14/43504 |

FOREIGN PATENT DOCUMENTS

| | | |
|---|---|---|
| EP | 2186521 A1 | 5/2010 |
| WO | 88/04671 A1 | 6/1988 |
| WO | 96/38186 A1 | 12/1996 |
| WO | 01/60874 A1 | 8/2001 |
| WO | 03/061672 A1 | 7/2003 |
| WO | 2009059350 A1 | 5/2009 |
| WO | 2016077879 A1 | 5/2016 |

OTHER PUBLICATIONS

Hampson et al., "Evaluation of a novel antimicrobial polymer for the control of porcine postweaning colibacillosis", Aust. Vet J., vol. 78, No. 2, Feb. 2000.

Pirrone et al., "A Styrene-alt-Maleic Acid Copolymer Is an Effective Inhibitor of R5 and X4 Human Immunodeficiency Virus Type 1 Infection", Journal of Biomedicine and Biotechnology, pp. 1-11, 2010.

Wang et al. "Cationic Phenylene Ethynylene Polymers and Oligomers Exhibit Efficient Antiviral Activity", Applied Materials and Interfaces vol. 3, No. 7, pp. 2209-2214, 2007.

Gupta et al., "Polyethylene glycol 4000 (PE4) as potential antiviral agent against Chandipura virus", Journal of Pharmacy Research, vol. 5, No. 3, pp. 1605-1607, 2012.

Supplemental European Search Report dated Oct. 8, 2019, in connection with European Application No. 17752574.

Liu (Robbins and Cotran Pathologic Bases of Disease, Kumar, V., et al., eds., 7th ed., chapter 17, p. 8, 797, 798, and 815 (2005)).

Mayo Clinic (Bacterial vs. viral infections: How do they differ?, https://www.mayoclinic.org/diseases-conditions/infectious-diseases/expert-answers/infectious-disease/faq-20058098 (2020)).

Kaiser Permanente (Antibiotics and common illnesses, https://wa.kaiserpermanente.org/healthAndWellness/index.jhtm?item=%2Fcommon%2FhealthAndWellness%2Fmedications%2FmanagingMedications%2Fantibiotics.html (2020)).

Kroschwitz (Concise Encyclopedia of Polymer Science and Engineenng John Wiley & Sons, p. 12 (1990)).

* cited by examiner

ANTI-VIRUS AGENT AND METHOD FOR TREATMENT OF VIRAL INFECTION

This is an application filed under 35 USC 371 based on PCT/AU2017/050139 filed 17. Feb. 2017, which in turn is based on AU 2016900595 filed 19. Feb. 2016 and AU 2016902715 filed 11. Jul. 2016. The present application claims the full priority benefit of these prior applications and herein incorporates by reference the full disclosures of these prior applications.

FIELD

The invention relates to a method of treatment of viral infection, particularly parenteral viral infection, using a copolymer comprising an acrolein-derived segment and a polyalkylene glycol oligomer segment wherein the copolymer has a molecular weight of up to 1500 Daltons, preferably up to 1000 Daltons, and to a process for the preparation of the copolymer by polymerization of acrolein in an aqueous solution of the polyalkylene glycol.

BACKGROUND

Viruses having a lipid envelope or coat-usually hydrophobic, are important human and animal pathogens. Examples of conditions associated with such viruses include Orthomyxoviruses (influenza viruses), HIV, Hepatitis, Ross River and Herpes. The Herpes viruses cause both primary and secondary infections that range from trivial mucosal ulcers to life threatening disorders in immuno-compromised patients. The Herpes group includes HSV-1, HSV-2, Herpes Zoster (chicken pox/shingles), HCMV (human cytomegalovirus), Epstein Barr Virus (EBV), Herpes 6, 7 (Roseola, post transplant infections) and Herpes 8 (associated with Kaposi sarcoma).

Persons infected with a Herpes type virus are typically subjected to cycles of outbreaks where symptoms are experienced and asymptomatic latent periods. During the latent periods, the virus resides in the ganglia where it is inactive and the patient is asymptomatic. However, although asymptomatic, a patient may still be able to infect others. This is known as viral shedding. Reoccurrence of symptoms can occur when the virus is reactivated. Reactivation can be triggered by many different events and is particularly problematic in immunocompromised patients.

There is a need in the art for alternative antiviral therapies. The present invention in one set of embodiments addresses these needs and provides for methods of treating viral infection.

Acrolein is extremely damaging to body tissues due to its high reactivity. Connections exist between acrolein gas in the smoke from tobacco cigarettes and the risk of lung cancer (Feng, Z; Hu W; Hu Y; Tang M (October 2006). "*Acrolein is a major cigarette-related lung cancer agent: Preferential binding at p53 mutational hotspots and inhibition of DNA repair*". Proceedings of the National Academy of Sciences 103 (42): 15404-15409). Pure polyacrolein, alone is not known to exhibit significant antiviral activity. However, a number of patents including U.S. Pat. No. 5,290,894, Melrose et al., disclose the preparation and uses of modified polyacroleins as potential antiviral agents for treatment of viral infection via the gastrointestinal tract. Further examples of polyacrolein of this type are described in U.S. Pat. Nos. 6,723,336, 7,629,002 and 9,119,394. Acrolein is an extremely reactive monomer and when polymerized, rapidly forms a high molecular weight intractable network. Normally, anionic polymerizations are conducted in a solvent free of water and provide rapid polymerizations to form high molecular weight polymers.

One of the perceived advantages of the polymers described in the prior art is that they cannot penetrate the gut wall so that their activity is confined to the gastrointestinal tract. U.S. Pat. No. 9,119,394 (Melrose) describes a polyacrolein polymer which may be formed by base catalyzed polymerization of acrolein and/or its acetal with an alkanol. The polymers have the advantage of a reduced propensity to migrate through membranes, specifically the membrane of the gastrointestinal tract.

U.S. Pat. No. 6,060,571 (Werle et al.) describes acrolein releasing polymers which release sufficient acrolein to provide activity as sanitizing agents in water systems. Such polymers are not suitable for use in vivo due to the toxicity of the significant levels of acrolein released in aqueous media.

The discussion of the background to the invention herein is included to explain the context of the invention. This is not to be taken as an admission that any of the material referred to was published, known or part of the common general knowledge as at the priority date of any of the claims.

SUMMARY

We have now found that low molecular weight copolymers comprising an acrolein-derived segment and polyalkylene glycol oligomer segment may be prepared so as to limit the molecular weight of the copolymer to no more than 1500 Daltons, preferably no more than 1000 Daltons. Further we have found that the low molecular weight copolymers provide potent anti-virus activity and may be used for treatment of parenteral viral infection, without release of acrolein monomer. Indeed the activity is enhanced when compared with acrolein polymers of higher molecular weight.

According to one set of embodiments, there is provided a method for the treatment, control or prophylaxis of a viral infection in a subject, the method including administering to the subject a copolymer comprising an acrolein-derived segment and a polyalkylene glycol oligomer segment (preferably of molecular weight of from 200 to 600 Daltons), the copolymer having a molecular weight of no more than 1500 Daltons, preferably no more than 1000 Daltons.

According to a further set of embodiments there is provided a method of treatment of viral infection (preferably a parenteral viral infection) in vivo comprising the step of contacting at least one target infected cell in vivo with an effective amount of a copolymer comprising an acrolein-derived segment and a polyalkylene glycol oligomer segment, the copolymer having a molecular weight of no more than 1500 Daltons, preferably no more than 1000 Daltons.

The viral infection may be caused by a range of viruses such as coated viruses (e.g. lipid coated viruses) including herpes, HIV, cytomegalovirus and influenza. Preferably, the viral infection treated and/or controlled by the method of the invention may be HSV-1, HSV-2, Vadcella Zoster Virus (in the form of chicken pox or shingles), HCMV, EBV, Herpes 6, Herpes 7 and Herpes 8.

In another embodiment the virus is influenza virus such as influenza A.

In yet a further embodiment the virus is Ross River virus.

The method of the invention may be particularly suitable for the treatment of viral infections in an immunosuppressed individual. The method of the invention may also be used as an adjunct therapy with other anti-viral therapies.

In yet a further aspect there is provided a process for preparation of a copolymer comprising an acrolein-derived segment (such as a polyacrolein oligomer) and a polyalkylene glycol oligomer comprising copolymerizing acrolein and polyalkylene glycol oligomer under conditions of alkaline catalysis of pH no more than 12.0 and within a pH range of 12.0 to 7.0 in an aqueous solution comprising at least 20% w/w water, and the polyalkylene glycol oligomer (preferably of molecular weight of from 200 to 600 Daltons) in a weight ratio of polyalkylene glycol/acrolein of at least 4, preferably at least 10.

Definitions

The term "body" means the body of humans and/or animals; the term "subject" means such a body which is the subject.

Intravenous therapy (IV therapy or iv therapy in short) is the infusion of liquid substances directly into a vein.

As used herein, the term "parenteral" means taken into the body in a manner other than through the intact digestive canal. That is, not within the normal stomach or intestine; not intestinal.

The term "parenteral viral infection" refers to a viral infection contracted in the body not within the gastrointestinal tract.

The term "pulmonary administration" refers to administration of a formulation of the invention into the lungs by inhalation.

As used herein, the term "inhalation" refers to intake of air to the alveoli of the lung. In specific examples, intake can occur by self-administration of a formulation of the invention while inhaling, or by administration via a respirator, e.g., to a patient on a respirator. The term "inhalation" used with respect to a formulation of the invention is synonymous with "pulmonary administration."

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject copolymer and/or composition from one organ, or portion of the body, to another organ, or portion of the body. Each carrier must be "acceptable" in the sense of being compatible with the other ingredients of the formulation and not unduly injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The copolymer may be used in a therapeutically-effective (or "pharmaceutically-effective or active") amount to provide treatment. The amount will depend on the mode of administration such as oral, intramuscular, intravenous, inhalation or transdermal administration. The phrase "therapeutically-effective amount" as used herein means that amount of a copolymer and/or a composition, material, or composition comprising the copolymer composition which is effective for producing some desired anti-viral therapeutic effect.

The term acrolein-derived segment refers to the copolymer segment comprising one or more acrolein monomer residues.

The terms oligomer, polyalkylene glycol oligomer and polyacrolein oligomer refer to polymers consisting of at least two monomer units, preferably at least three monomer units. The oligomers will typically comprise from 2 to 20 monomer units; in one embodiment the number of units is from 2 to 10.

The terms "monomer units" and "monomer residues" refer to units present in the copolymer derived from the reacting monomers such as acrolein and polyalkylene glycol.

The polydispersity index is the ratio of the weight-average molecular weight ($M_w$) of the polymer to the number-average molecular weight ($M_n$) of the polymer. The weight-average molecular weight and the number-average molecular weight of a polymer can be determined by analytical methods, such as high performance liquid chromatography. Once the weight-average and number-average molecular weights have been determined, the polydispersity index is easily calculated by dividing the weight-average molecular weight by the number average molecular weight, $M_w/M_n$. A hypothetically monodisperse polymer has a polydispersity index of 1.000. However, typical commercial polymers, such as the commercially available resins, have a polydispersity index of 10 or more. Polymers with broad molecular weight distributions have higher polydispersity indices and polymers with narrow molecular weight distributions have lower polydispersity indices.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

BRIEF DESCRIPTION OF DRAWINGS

Embodiments of the invention are described with reference to the Drawings. In the drawings.

DETAILED DESCRIPTION

Figure 1:
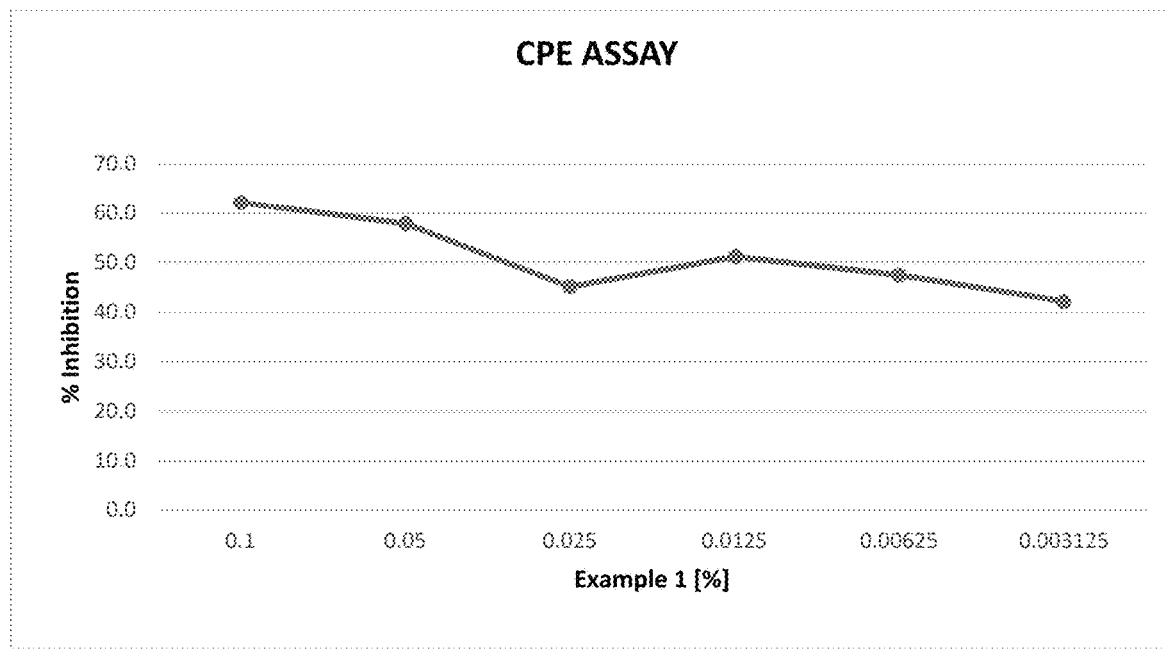
FIG. 1 is a graph showing the CPA assay results of variation in % inhibition with concentration as described in Example 3.
Figure 2:
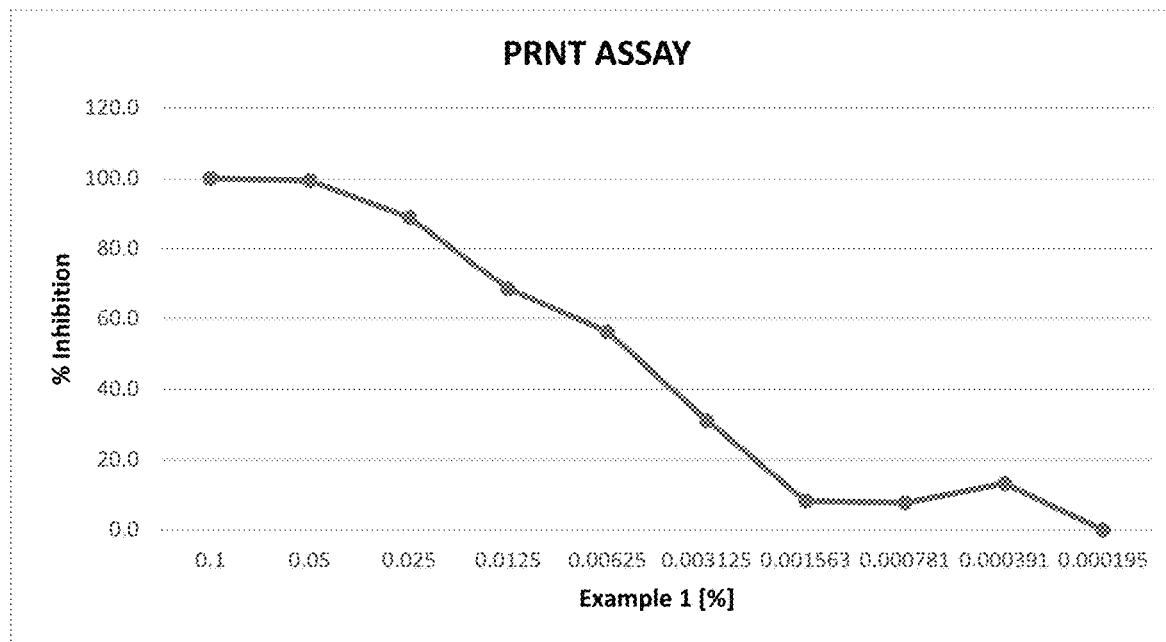
FIG. 2 is a graph of the PRNT assay results of variation in % inhibition with concentration (%) of the formulation of Example 1 as set out in Example 3.

The method of treatment comprises administering a copolymer comprising segment and a polyalkylene glycol oligomer segment (preferably of molecular weight of from 200 to 600 Daltons), the copolymer having a molecular weight of no more than 1500 Daltons, preferably no more than 1000 Daltons.

The acrolein-derived segment may comprise one or more acrolein monomer residues. In one embodiment the acrolein-derived segment comprises a polyacrolein oligomer.

The polyalkylene glycol may be a poly($C_1$ to $C_4$ alkylene glycol) or mixture or copolymer thereof but in general the polyalkylene glycol is most preferably a polyethylene glycol, preferably of molecular weight in the range of from 200 to 600 Daltons.

It will be understood by those skilled in the art that the term polyethylene glycol preferably does not include diethylene glycol. Polyethylene glycol of average molecular weight 200 to 600 Daltons includes polyethylene glycol of nominal average molecular weight 200 to 600 Daltons wherein the average molecular weight is not more than 110% and not less than 90% (preferably not more than 105% and not less than 95%) of the nominated value. Polyethylene glycol is of formula H—[$OCH_2CH_2$]$_n$—OH. The average value of n is at least 3 and is generally from 3 to 13 (although the average need not be an integer). Polyethylene glycol is widely available from commercial suppliers in pharmaceutical grades and is sold in specified nominal molecular weights which generally signify that the average molecular weight is not more than 105% and not less than 95% of the nominated value. The viscosities and methods for molecular weight determination are disclosed in USP NF Official Compendium of Standards Volume 11180-1182 [2007 Edition]. In one set of embodiments the polyethylene glycol is of molecular weight from 200 to 400. In some embodiments it may be preferred to use a specific pure oligomer of ethylene glycol such as the compound of formula H—[$OCH_2CH_2$]$_n$—OH where n is 3 or 4.

In one set of embodiments the molecular weight (always meaning herein, the number average molecular weight) of the copolymer is at least 300 Daltons preferably at least 400 Daltons such as in the range of from 400 to 1500 Daltons and more preferably the molecular weight is in the range of from 400 to 1000 Daltons.

The treatment may be prophylactic or curative.

In another embodiment the copolymer is administered systemically, for example, by oral administration, inhalation, transdermal delivery or by injection such as into the blood stream or intramuscular injection or by intravenous therapy such as by injection or infusion. It is generally accepted that molecules of molecular weight no more than about 1000, particularly less than about 800 Daltons have reasonably free passage across the abdominal membranes. Oral administration requires that the copolymer is absorbed through the gut wall and into the systemic circulation. In this embodiment it is particularly preferred that the copolymer administered orally is of molecular weight no more than 1000 Daltons such as a molecular weight in the range of from 400 to 800 Daltons. We have found that copolymers of this molecular weight, when administered orally, are transported into the systemic circulation to provide treatment of parenteral viral infection. The proportion of the copolymer absorbed through the gut wall is generally greater for copolymers of lower molecular weight in this range.

The copolymer may be applied as an aerosol, gel, topical foam or ointment or impregnated into a dressing for application to skin or mucous membranes for transdermal or transmucosal delivery. The copolymer may be applied as an inhalation via an aerosol or the like.

In a further embodiment the copolymer is administered by transdermal delivery from a composition which may comprise a penetration enhancer for the polymer. Patches, microneedles or like devices may be used to enhance transdermal delivery.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In another preferred embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

The copolymer may be formulated in an aqueous composition as it is soluble and remains soluble over the full 1 to 14 range of pH. The copolymer may be administered in compositions with known pharmaceutically-acceptable carriers and excipients; however aqueous formulations provide a significant advantage. The composition may comprise a wide range of concentrations of the copolymer depending on the specific virus to be treated and mode of administration. In one set of embodiments the concentration of the copolymer in an aqueous pharmaceutical composition is in the range of from 0.01% by weight to 20% by weight of the composition. Accordingly, in a preferred set of embodiments the copolymer is administered as an aqueous solution.

The composition may be administered orally in the form of a tablet, caplet, syrup or liquid and the dose administered orally will depend on the severity and type of virus but may be in the range, for example, of from 1 mg to 1000 mg per kilogram of bodyweight per day, such as from 10 mg to 500 mg per kilogram of bodyweight per day.

The finding herein that acrolein-copolymers are active against parenteral disease was not expected, due to the mechanism of action believed to relate to their activity. U.S. Pat. No. 6,723,336 uses added protein to totally quench the antimicrobial activity of acrolein-polymers. The focus of the prior art has been to treat infections in the gastro-intestinal tract by oral administration of acrolein-polymers having sufficiently high molecular-weights so as to prevent their trans-intestinal migration. Indeed the reactivity of acrolein monomer is such that it has not heretofore been considered to be feasible to polymerize acrolein so as to yield products having molecular weights no more than about 1,000 Daltons. Administration against parenteral disease has also been deliberately avoided for reasons of their potential toxicity (including reaction with serum proteins).

In the prior art preparation of polyacrolein it was considered that the mechanism of polymerization was anionic, and that water content needed to be minimized to avoid quenching of the anion or dissociation of the product. We have found that the molecular weight may be limited to 1000 Daltons or lower by controlling the ratio of monomers, the dilution of acrolein and polyethylene glycol with water and compared to prior art, keeping the pH in a lower range-maintaining the pH at no more than 12.0 and preferably within a pH range of 12.0 to 7.0. That is, to achieve the new mechanism of polymerization, the pH range is dropped two whole pH units, or 100-fold lower hydroxyl-ion concentration than ever used in prior art polymerizations.

In one set of embodiments the invention provides a method for preparation of a copolymer for treatment of a parenteral viral disease the process comprising base catalyzed polymerization of acrolein in an aqueous solution comprising polyethylene glycol (preferably of molecular weight of from 200 to 600 Daltons) wherein the ratio of polyalkylene glycol/acrolein is at least 4, preferably at least 8, more preferably at least 10, and water is present in an amount of at least 20% by weight of the composition.

In a preferred set of embodiments the process comprises adding an aqueous solution of acrolein, preferably having an acrolein concentration of no more than 50% w/w, to an aqueous solution of polyethylene glycol comprising at least 10% w/w water and having a pH of no more than 12.0, preferably no more than pH 11.

In a still more preferred embodiment acrolein is added as an aqueous solution to an aqueous solution of polyalkylene glycol of pH 9 to 11.

In general we have found that in the aqueous systems used in the process, a relatively low pH such as no more than 12.0 such as not more than 11.5 (preferably no more than 11) provides significant advantages over the prior art pH range up to pH 14 used to polymerize acrolein. Relatively high pH, as used in the prior art for extended periods, provides oxidation and introduces carboxyl groups which improve solubility. In contrast we have found that solubility is provided in the process of the invention without the need for extended heating at relatively high pH and as a result the carbonyl and/or carboxyl content is very low, typically 0-10% of the copolymer. The minimum carbonyl or carboxyl content is believed to minimize both unwanted reaction with proteins of miscellaneous origins or repulsion to acidic and anionic coatings of germs, thereby in both cases, enhancing antibiotic action.

Without wishing to be bound by theory it is believed that in the process of the present invention polymerization of acrolein in the presence of alkali does not proceed by a totally anionic mechanism in the presence of such significant amounts of water but rather has a significant free-radical mechanism of polymerization.

This conclusion is supported by the facts that: (a) Polymerization was facilitated by the presence of the dual free-radical, oxygen (b) Water which is a major component of the solvent, is anion-quenching (c) Polymerization is significant at ambient temperatures and above-fast, exothermic and inhibited by the typical free-radical inhibitor, hydroquinone-all observations being typical of free-radical polymerization, rather than ionic polymerization (Florey; Odian). Again, without wishing to be bound by theory, it is believed that the reaction mechanism involves formation of initiator-radical between oxygen and hydroxyl ion, followed by radical transfer to polyethylene glycol solvent, thus initiating polymerization; then solvent-transfer termination involving solvent-hydroxyl to limit the number of acrolein residues polymerized at the active radical site, adjacent to the carbonyl within the copolymer.

The polyalkylene glycol oligomer is believed to provide chain-transfer and/or chain-termination, thereby limiting, (together with the aqueous dilution), the molecular weight in direct proportion to the overall hydroxyl-content.

In overview, the core-strategy of the synthesis- and different from that of the prior art U.S. Pat. No. 9,119,394, is to cause the two segments of the resulting co-polymeric product to be joined by a mechanism which is believed, without wishing to be bound by theory, to proceed by a free-radical mechanism, rather than by a nucleophilic Michael addition. This is done by maximizing the formation of propagating free-radical active-centres (by maximizing the presence of the radical, oxygen)- and by minimizing pH, minimizing the formation of hydrogen-ion deficient active-centres for nucleophilic Michael addition.

The active copolymer was shown by HPLC to have insignificant reaction with either of the amino-acid models cysteine (sulfhydryl) or threonine (hydroxyl), and that the anti-disease activities of the copolymers can be attributed to a non-covalent, physical hydrophobic effect alone, at the identified proximate carbons within the copolymers, upon the stability of target cell membranes. The mechanism of action in the prior art, which relied on chemical reaction of carbonyl groups in modified polyacrolein with protein, is not therefore believed to be responsible for the anti-virus activity of the present copolymers.

In contrast with the prior art which teaches the destructive reactivity of acrolein polymers with protein, we have found that the anti-virus activity of the copolymer is not significantly depressed by the presence of protein. We have found that the anti-virus activity of the copolymers are sufficiently fast so as to more than compete with any intra-vascular chemical reactions with protein leading to toxicity, or with in vivo clearing processes. In the perspectives of prior art, consistently, these observations and conclusion are counter-intuitive to progressing to synthesize and then use the copolymer (such as the copolymer of Example 1) parenterally, as herein.

The copolymers disclosed herein represent a much-less toxic intra-vascular challenge than acrolein-polymers from prior art. We have found that the copolymers may be prepared with a low polydispersity and that a low polydispersity of preferably less than 5, more preferably less than 2, and most preferably less than 1.5, still more preferably less than 1.2, enhances the performance of the copolymer, particularly where the molecular weight is less than 1000, such as from 400 to 1000 Daltons, more preferably 400 to 800 Daltons such as 400-600 Daltons. The polymers of the present invention may be prepared as a narrow symmetrical and single polymer with polydispersity index of approximately 1. Previously described acrolein polymers generally contain a higher polydispersity, or in the case of the polymer of Example 6 of WO 09/059350, contain, on very sensitive UV detection, about 1% and about 8 times more of a wide range of lower molecular weight polymers/residues, which are not readily detectable from refractive index detection. The copolymers herein may be formed quantitatively, in narrow molecular weight distribution of polydispersity near unity. The copolymers contain much fewer potentially toxic contaminants (side-products and starting materials, including residual, lachrymatory acrolein) than heavily heated and autoxidized acrolein-polymers of earlier art. In the preferred embodiment of the invention, both carbonyl content and the pH used in preparation by base catalyses are at an unprecedented minimum- and both factors may be used to minimize side-products and their potential toxicity from particularly, Cannizarro reaction with carbonyl, and which prior art has found to be abnormally rapid in acrolein-polymers.

The copolymer has been found to have active anti-virus activity. This represents a new, general and successful method of treatment of viral infection in a subject.

In addition to acrolein monomer, other monomers e.g., acrylic acid, acrylamide, acrylonitrile, vinyl chloride, styrene, methacrylic acid, methyl methacrylate, vinyl acetate, vinyl pyridine and vinyl pyrrolidone may be used as additional monomers in preparation of copolymers comprising a polyalkylene glycol oligomer segment and acrolein-derived segment, as described herein. The additional monomers may be present in amounts, which are not adverse to the anti-virus activity of the copolymer. The ratio of monomers may be chosen so as to maintain the water solubility of the copolymer and incorporation of other monomers may be controlled by reaction conditions and relative monomer concentrations bearing in mind monomer reactivity. In general it is preferred that other monomers constitute no more than 15 mole % of the monomer residues of the copolymer, preferably no more than 10 mole % and most preferable the copolymer only consists of polyalkylene glycol and acrolein monomer residues.

The hydrophobic mechanism, which is characteristic of the copolymers of the invention, is achieved through the process steps, which provide control over: molecular weight; affinity for anti-virus-reaction with virions and cells infected with virus; enhanced anti-virus activity in the presence of protein; and minimization of both carbonyl and carboxyl-contents within the copolymers.

The copolymer anti-virus provided herein generally provide efficacy against a wide range of types of virus, whether resistant or non-resistant to other chemotherapies.

In a preferred set of embodiments the method of preparation of copolymers of the present invention comprises the following steps:

providing a mildly basic (preferably of pH no more than 12.0; more preferably of pH 9 to 11) aqueous solution of a polyalkylene glycol (preferably polyethylene glycol of molecular weight in the range of from 200 to 600 Daltons);

stirring the mildly basic solution vigorously to entrain air;

adding (preferably slowly over a period such as at least 2 minutes, more preferably at least 5 minutes) acrolein as an aqueous solution of concentration no more than 50% w/w of the acrolein aqueous solution (usually containing preservative);

maintaining the reaction temperature in the range of from 10° C. to 40° C.;

and once the acrolein monomer has been consumed, adding acid to provide a pH less than 9 and preferably no more than 8.

The molecular weight of the resulting copolymer is controlled by the molecular weight of the polyalkylene glycol, as well as being directly proportional to its hydroxyl concentration. (The polymerization begins at ambient temperature, then rises slightly as the exothermic polymerization-which is evident from the appearance and then disappearance of yellow color from the preservative, progresses.)

During the reaction the stirring is preferably continued, and the pH maintained mildly basic (preferably of pH no more than 12.0, more preferably of pH 9 to 11), only as necessary. The addition of more base and its concentration is minimized so as to lower degradation/side-reactions and to reduce carbonyl or carboxyl formation in the product.

Finally, the pH of the solution may be reduced. In a preferred set of embodiments, the pH is adjusted to near neutral, by the addition of acid. The extremely pungent smell of acrolein is no longer evident in the copolymer product, which is generally formed in at least 99% yield.

The resulting acrolein-copolymers typically have molecular weights in the range of from 250 to 1000 Daltons (such as 300 to 1000 Daltons, 400 to 1000 Daltons or 400 to 800 Daltons). The copolymers are free of turbidity which would be expected from any content of polyacrolein. Content of, and bonding between the acrolein-derived segment and the polyethylene glycol oligomer segment, in the manner proposed earlier, is demonstrated by the size separation-HPLC of all copolymers-each having one-single, narrow, symmetrical, dominant and unresolvable mass-peak-without indicating either residual acrolein monomer or substantial polyacrolein; furthermore, the copolymer MW 1,000 from Example 2, contrary to the resolvable change and expectation if the association between the segments was merely physical inter-adsorption-did not change in size separation-HPLC, nor anti-virus activity, after equilibration with polyethylene glycol MW 200 under basic conditions comparable to those used in the original preparation of all the copolymers. (See Example 2).

The weight-ratio of acrolein:polyethylene glycol used in its preparation of the copolymer is preferably between 1:4 and 1:40, and more preferably between 1:8 and 1:20.

The preferred base is an aqueous solution of an alkali hydroxide; more preferably, the alkali hydroxide is sodium hydroxide.

The preferred acid is dilute hydrochloric acid—although acetic acid is useful for pH buffering purposes.

It is preferred that the addition of acrolein to the aqueous solution of polyalkylene glycol takes about 10 minutes- and the reaction to completion, generally takes place about 40 minutes, and preferably is no more than 90 minutes.

Typically we have found that a reaction time of 50 minutes is suitable to obtain virtually complete conversion to the copolymer product.

The acrolein is preferably added to the aqueous polyalkylene glycol as an aqueous solution-more preferably as a concentration in the range of from 10% to 30% by weight of acrolein monomer, based on the weight of the aqueous acrolein solution to be added to the aqueous polyalkylene glycol solution.

The resulting copolymer has a reactive carbonyl group-content (plus any carboxyl-content) of less than 10%, more preferably less than 5%, and still more preferably zero %.

The acrolein solution usually contains inhibitor, hydroquinone such as no more than 0.5% and typically 0.01 to 0.5% and more preferably 0.1% w/w.

It will be apparent to those in the art that the copolymers herein may be included in a variety of compositions and physical forms. Particularly, compositions and pharmaceutical methods of use, in vivo, will be apparent, taking advantages of slower clearances of the copolymer. Also, it will be apparent that pharmacological advantage may be taken of variance in molecular weight to adjust the rate of penetration through membranes, tissues and organs- and the resultant absorption or distribution within human or animal body; in this context, the lower molecular weight copolymers such as, for example 300 to 800 Daltons are more rapidly absorbed and distributed than copolymers over a molecular weight of 1000 Daltons.

In view of the results herein, it is also conceivable to add protein, particularly broth to enhance in-use anti-virus activity of the copolymers.

The subject products, herein, are aqueous-soluble and administration to humans/animals may be by the usual methods known in medicine-particularly, by mouth or injection- and are able to be used in any practical pharmaceutical way, alone or in compositions, within organs and tissues, or in contact with or in in vivo vascular systems of either humans or animals. When the copolymers are administered to humans and animals, they can be given per se or as a pharmaceutical composition containing, for example, 0.1% to 99.5% (more preferably, 0.5% to 90%) of active ingredient in combination with a pharmaceutically-acceptable carrier.

Compositions may be solids, solutions, gels, emulsions or suspensions of matter comprising a pharmacologically effective amount of the copolymer. The compounds of the invention can be used in combination with one or more other chemotherapeutic agents. The dosage of the inventive compounds may be adjusted for any drug-drug reaction. In one embodiment, the chemotherapeutic agent is selected from the group consisting of mitotic inhibitors, alkylating agents, anti-metabolites, cell cycle inhibitors, enzymes, topoisomerase inhibitors such as CAMPTOSAR (irinotecan), biological response modifiers, anti-hormones, antiangiogenic agents such as MMP-2, MMP-9 and COX-2 inhibitors, anti- androgens, platinum coordination complexes (cisplatin, etc.), substituted ureas such as hydroxyurea; methylhydrazine derivatives, e.g., procarbazine; adrenocortical suppressants, e.g., mitotane, aminoglutethimide, hormone and hormone antagonists such as the adrenocorticosteriods (e.g., prednisone), progestins (e.g., hydroxyprogesterone caproate), estrogens (e.g., diethylstilbesterol), antiestrogens such as tamoxifen, androgens, e.g., testosterone propionate, and aromatase inhibitors, such as anastrozole, and AROMAS IN (exemestane).

The copolymers and their compositions have substantial activity against virus.

Without wishing to be bound by theory, the mechanism of action provides advantages:

that the copolymer described by this invention depends upon a non-specific, hydrophobic reaction between the copolymer and the proteins of the outer membranes of diseased cells- the reaction will be greater, the greater the hydrophobicity of the outer membranes of the cells and the metabolic activity weaken the cells which increases internal osmotic pressure-greater than in surrounding cells;

that the reaction weakens the membranes.

Therefore, the cells having greater internal metabolic activity will have greater internal osmotic pressure, and greater outward pressure upon the outer membranes, giving comparatively greater sensitivity to rupture from the effect of the copolymers.

This hypothesis has been put to testing and found successful. Furthermore it is general i.e., not specific and applicable to cells containing virus of all types.

It will be apparent to those in the Art that the metabolic activity, osmotic pressure and membrane-tension of cells containing virus especially, will be greater than in surrounding cells- and the outer membranes will be more sensitive to the polymer described by this invention.

It is also known by those in the Art that bacterial infections may lead to cancer, due either to the infection causing chronic inflammation, or the infection releasing cancer-inducing metabolites (*Helicobacter pylori* leading to cancer is a well-known example). Thus, as the copolymer described within this invention has already been found to be practical as an antibiotic drug against bacteria, its virus and cancer activities as described here, should be advantaged and possibly synergistic. Also, as viral infection, particularly by influenza viruses is often associated with bacterial infection as well-again, concurrent anti-viral and anti-biotic properties in the one drug are advantageously synergistic.

It will also be apparent that as Example 1 has the same or similar resultant extent of antibacterial activity against bacteria, irrespective of whether mutation has taken place to form a superbug/resistant form of it- the same insensitivity to form occurs here i.e., the same propensity occurs irrespective of whether the virus is in a super (resistant) form, usually evolved through mutation.

It will also be apparent that other antibiotics (antibacterials), antiviral drugs than those described here may be considered for addition to formulations of the copolymers, so as to achieve added pharmaceutical effects.

The invention will now be described further with reference to the following Examples. It is to be understood that the examples are provided by way of illustration of the invention and that they are in no way limiting to the scope of the invention.

EXAMPLES

The copolymers from Example 1 and Comparative Example 1 have anti-virus characteristics. The lower MW 500 from Example 1-in vivo always-has been found to be more effective than higher molecular weight polymers of acrolein and PEG.

Estimates of Carbonyl Content

The estimates of carbonyl content reported herein are based upon an established method (Peters 1962; Melrose 2009). In duplicate, an aqueous sample-solution of copolymer (1 g) was weighed to an accuracy of 0.01 g-water (9 g) was added, and then the solution was brought to pH 6.00 by the addition of either 0.01M hydrochloric acid or 0.01M aqueous sodium hydroxide, as appropriate.

A 1% solution of hydroxylamine hydrochloride (50 mL) was brought to pH 6.00 with 0.01M aqueous sodium hydroxide.

The above solutions of copolymer and reagent were mixed, and stood at room-temperature for 30 minutes; the reactants were then back-titrated with 0.01M aqueous sodium hydroxide (V mL) to pH 6.00.

Thus, the w/w % carbonyl-content of the original sample-solution (W g) was estimated as acrolein, equals: $V \times 0.10 \times 5.6/W$.

Quantitative Analysis of Copolymer by HPLC

High Performance Liquid Chromatography (HPLC) was performed on Shimadzu Prominence equipment using simultaneously, both refractive-index and UV (268 nm) detectors; the column was either or both (in series) Waters Hydrogel 120 or Waters Hydrogel 250, for separation by size-exclusion.

MW calibration was done by a straight-line plot of exclusion-time versus log MW of Sigma-Aldrich polyethylene glycols of average MW range 200 to 10,000 Daltons. Thus, it follows from the method of determination that the molecular weights of acrolein-copolymers which were always determined on this basis and reported herein-always refer to a Number Average Molecular Weight (corrected to the nearest 500 Daltons).

Separations were performed on aqueous solutions of solute (0.020 mL; 0.4% w/w), with water-solvent (0.6 mL to 1.0 mL/minute).

Quantitative Analysis of Copolymer by Mass Spectrometry

Two separate techniques (by courtesy of Shimadzu Scientific Instruments (Oceania) Pty Ltd) were performed:

Direct injection into the mass spectrometer, without prior chromatography;

Mass spectrometry, after prior chromatography

Equipment; experimental conditions were: Nexera UHPLC Binary High Pressure Gradient, and LCMS-8060 (run under Q3 scans to simulate single quadrupole mass spectrometry; mobile phase equal parts 0.02% formic acid in water, and 0.02% formic acid in acetonitrile, and column Phemonenex Aeris XB C18 300 A 150×2.1 mm.

Quantitative UV/Visible Analysis of Polymer Solutions

Solutions for analysis were prepared by dilution of copolymer (250 mg) in water (20 g) and then if applicable, a stoichiometric molar equivalent of reactant; then, diluted 1:9 with water before taking the UV spectrum on Shimadzu UVmini-1240 equipment.

Example 1 and Comparative Example 1

Example 1 describes preparation of a copolymer of the invention of molecular weight of about 500 Daltons, comprising a polyacrolein oligomer segment, and a polyethylene glycol oligomer segment of molecular weight 200 Daltons. The copolymer is purposefully illustrated from a preparation at pH 12.0, as this is the highest pH recommended for reliable success, without introducing levels of unwanted side-reactions as described herein. The anti-virus activity of the copolymer are generally higher compared with that of a corresponding copolymer of molecular weight approximately 2500 Daltons.

Example 1-Preparation of Copolymer of MW about 500 Daltons

A solution of freshly distilled acrolein (5 g; inhibited with hydroquinone 0.1% A w/w) in water (20 g) was slowly added over 10 minutes to a solution of water (20 g) and polyethylene glycol (60 g; MW 200) which had been rendered pH 12 by the addition of 1M aqueous sodium hydroxide; during the 10 minutes, the yellow color of oxidized hydroquinone quickly appeared, then disappeared. During the process the composition was continuously and vigorously stirred to provide copious contact with air. An exothermic and rapid polymerization took-place, and the temperature of the reactants was maintained between approximately 25° C. and 35° C.

After another 50 minutes, the clear solution was adjusted to pH 7.5 by the addition of 1M aqueous hydrochloric acid; the product was a clear, almost colorless (very pale yellow) solution. All the tests done on the sample and the results herein, were done on a sample without any purification and having been stored for 4 or 6 years at 7° C.; this is taken as indicative of the high purity and high stability of the product.

The UV-visible, 200-600 nM spectrum of the product only had substantial absorption in the far edge of the 200-300 nM region. This is consistent with negligible content of unsaturation conjugated with carbonyl and which may be associated with propensity for a Michael Reaction HPLC indicated the polymerization-yield was 99-100% w/w, and any residual acrolein-monomer was less than 1 ppm w/w; MW was approximately 500 Daltons. Mass spectrometry showed base a base-peak of 312, and indicating the copolymer comprised five oxyethylene (ex PEG) residues covalently joined linearly to two 2-propanal (ex acrolein) residues.

When tested down to pH 1 (and up to pH 14), the copolymer remained soluble. The copolymer has approximately 0-10% w/w carbonyl-content or carboxyl-content.

The single peak of the product in HPLC remained narrow and unresolved whether HPLC was done in water at 1 ml/minute, over Waters Hydrogel 120, Waters Hydrogel 250 singularly or in series of either, alternate sequence.

The same preparative results occurred when the polymerization was conducted at either pH 8 or pH 10, and always with exactly the same in vitro microbiological rate-results against *E. coli*, and same HPLC results (except pH 8 gave a product having an amount of materials indicative of dimers or oligomers of acrolein of total amount less than 1% w/w; in vivo microbiological rate tests were the same for all products.

The preparation of Example 1 was independently repeated a number of times, at various pHs between 8 and 12, including separately pH 8, pH 10 and pH 12 by another member of the applicants' laboratory, and gave identical polymerization results, HPLC and in vitro rate-test results against *E. coli*.

Comparative Example 1-Copolymer of Molecular Weight about 2500 Daltons

This Example describes preparation of a copolymer, not of the invention, of higher molecular weight, 2500 Daltons comprising a polyethylene glycol segment of molecular weight 2000.

A solution of freshly distilled acrolein (5 g; inhibited with hydroquinone 0.1% w/w) in water (20 g) was slowly added over 10 minutes to a solution of water (30 g) and polyethylene glycol (20 g; MW 2,000) which had been rendered pH 11 by the addition of 1M aqueous sodium hydroxide; during this period, the yellow color of oxidized hydroquinone quickly appeared, and then disappeared. The composition was vigorously mechanically stirred prior to and during addition to provide copious contact with air. An exothermic and rapid polymerization took place, with the temperature maintained between 25° C. and 35° C.

After stirring during an additional 50 minutes, the clear solution was adjusted to pH 7.5 by the addition of 1M aqueous hydrochloric acid; the product was a clear, almost colorless (very pale yellow) solution.

It is noteworthy that in common with all polyacrolein-products in prior art, agar-diffusion techniques of microbiological analysis are not used herein, due to resistance by relatively high molecular weight products to diffusion through agar.

All the tests done on the sample and their results recorded herein, were done on a sample without any purification and having been stored for 4 to 6 years at 7° C.; this is taken as indicative of the high purity and high stability of the product.

The UV-visible, 200-600 nM spectrum of the product only had substantial absorption in the far edge of the 200-300 nM region.

HPLC indicated the polymerization-yield was 99 to 100% w/w, and any residual acrolein-monomer was less than 1 ppm w/w; MW was approximately 2,500 Daltons. When tested down to pH 1 (and up to pH 14), the polymer remained soluble. The polymer has approximately 0-10% w/w carbonyl-content.

The single peak of the product in HPLC remained narrow and unresolved whether HPLC was done in water at 1 ml/minute, over Waters Hydrogel 120, Waters Hydrogel 250 singularly or in series of either alternate, sequence.

Based upon the polymerization mechanism described herein, It may be calculated that equivalents of acrolein monomer added in the polymerization (in relation to equivalents of polyethylene glycol) are greater in the case of Comparative Example 1, than Example 1, and therefore any propensity to form any insoluble polyacrolein is greater in the former, but was not observed, even after standing at 7° C./6 years. Stepwise acidification of a dilute solution of the acrolein-polymer to pH 2.5 with dilute hydrochloric acid-and back-titration with dilute sodium hydroxide solution demonstrated the absence of carboxyl groups ($pK_a$=4.5).

Both copolymers were still stable after four years at 8° C., and were stable to simulated pH conditions during residence time in the human stomach.

All observations were made between pH 6.5 and 7.0-this was quite naturally attained, and avoided the complications of possible interactions with a variety of added salts from different buffers.

Example 2

This example demonstrated preparation of a copolymer of the invention of molecular weight of about 1000 Daltons comprising a polyethylene glycol oligomer segment of molecular weight 600 Daltons.

A solution of freshly distilled acrolein (5 g; inhibited with hydroquinone 0.1% w/w) in water (20 g) was slowly added over 10 minutes to a solution of water (20 g) and polyethylene glycol (60 g; MW 600) which had been rendered pH 10 by the addition of 1M aqueous sodium hydroxide. The composition was vigorously stirred before and during the addition of acrolein to entrain air and provide copious contact with air, an exothermic and rapid polymerization resulted and the temperature was maintained between about 25° C. and 35° C. After commencement of the addition the yellow color of oxidized hydroquinone quickly appeared and then disappeared resulting in a clear solution.

After another 50 minutes, the clear solution was adjusted to pH 7 to 8 by the addition of 1M aqueous hydrochloric acid; the product was a clear, almost colorless (very pale yellow) solution. (The UV-visible, 200-600 nM spectrum of the product only had substantial absorption in the far edge of the 200-300 nM region.)

HPLC indicated the polymerization-yield was 99-100% w/w, and any residual monomer was less than 1 ppm w/w; MW was approximately 1,000 Daltons. When tested down to pH 1 (and up to pH 14), the copolymer remained soluble. The polymer has approximately 0-10% w/w carbonyl-content.

Polyethylene glycol MW 200 (120 mg) was added to the copolymer (383 mg), then one drop of 1M sodium hydroxide to bring the pH to 11; after standing at ambient temperature for 2 hours, the pH was adjusted to 7.5 with a drop of 1M hydrochloric acid, and stood 3 days. Neither the HPLC nor the anti-virus activity of the copolymer changed as the result of this treatment.

Example 3

Part 1 In Vitro Anti-Viral Evaluations of Example 1 Against Influenza A TX/36/91 (H1N1) Firstly, in a CPE Assay (and Cytotoxicity of the Antibiotic), and Secondly, in a PRNT Study.

The following two examples of in vitro activities of Example 1 are representative of instances when action is prophylactic/inside the cell- and action is curative/outside the cell, respectively.

CPE-Cytopathic Effect Assay-FIG. 1

MDCK cells were seeded in 96-well plates and incubated overnight

The next day cells were infected with IFV A/TX/36/91 at an MOI of 0.01 for 24 h at 35° C.

The following day serial dilutions of Example 1 (starting at 0.1% (1000 ppm) with 2-fold dilutions) were prepared in medium The inoculum was removed from the cells and the serial dilutions were added to the cells for 1 h at 35° C.

Compound dilutions were removed and cells were evaluated for viral antigens by ELISA.

Cytotoxicity Assay

MDCK cells were seeded in black-walled 96-well plates and incubated overnight

The next day growth medium was removed from the cells and incubation medium was added The following day serial dilutions of Example 1 were prepared as described for the CPE assay The medium was aspirated from the cells and the compound dilutions were added for 1 h at 35° C. Cells that were incubated with medium only were used for 0% cytotoxicity data Medium was aspirated and cells were lysed for evaluation of the ATP content on day 5 using Promega's CelltiterGlo kit The resulting luciferase luminescence was quantified and used to calculate the CC50 using 4-PL curve fit.

PRNA-Plaque-Reduction Neutralization Assay (and Cytotoxicity of the Antibiotic)-FIG. 2

Vero cells were seeded in 24-well plates and incubated overnight

The next day serial dilutions of Example 1 (starting at 0.1% (1000 ppm) with 2-fold dilutions) and the control antibody were prepared in medium The serial dilutions were incubated with 200 PFU of IFV A/TX/36/91 for 2 h at 35° C.

Afterwards the inoculum was added to the cells for 1 h at 35° C.

The inoculum was removed and the plates were incubated for 5 days

Virus titers were determined by immunoplaque assay

Cytotoxicity Assay

Vero cells were seeded in black-walled 96-well plates and incubated overnight

The next day serial dilutions of Example 1 were prepared as described for the PRNT assay The growth medium was aspirated from the cells and the compound dilutions were added. Cells that were incubated with medium only were used for 0% cytotoxicity data Compound was removed after 1 h and fresh medium was added before placing the plates at 35° C. for 5 days Medium was aspirated and cells were lysed for evaluation of the ATP content on day 5 using Promega's CelltiterGlo kit The resulting luciferase luminescence was quantified and used to calculate the CC50 using a 4-PL curve fit. The results are shown in Table 1.

TABLE 1

| DATA | | | | |
|---|---|---|---|---|
| | PRNT50 | | EC50 | |
| Formula 1 [%] | % Inhib. | SD | % Inhib. | SD |
| 0.1 | 100.0 | 0.0 | 62.2 | 8.9 |
| 0.05 | 99.4 | 0.9 | 57.9 | 10.5 |
| 0.025 | 88.9 | 0.0 | 45.1 | 7.9 |
| 0.0125 | 68.6 | 14.8 | 51.2 | 1.1 |
| 0.00625 | 56.3 | 9.6 | 47.5 | 6.9 |
| 0.003125 | 31.1 | 12.2 | 42.2 | 2.0 |
| 0.001563 | 8.2 | 11.5 | | |
| 0.000781 | 7.7 | 7.0 | | |
| 0.000391 | 13.2 | 13.1 | | |
| 0.000195 | 0.0 | 0.0 | | |

No cytotoxicity was observed between copolymer described as Formula 1 and either MDCK (canine) cells or Vero (monkey) cells.

Example 4-In Vivo Antiviral Evaluation-

This example examines the in vivo activity of the copolymer of Example 1 in control of viral infection, specifically influenza A TX/36/91 (H1N1).

A treated group of 10 mice "Group 1" were compared with an untreated group of 10 mice to examine the response to viral infection.

Group 1 (intravenously infected by intra-nasal administration; treated subsequently at a dose-rate of 140 mg/kg of mouse during each of the first 5 days with Example 1 70 mg/kg). Group 2 (intravenously infected by intra-nasal administration; not treated). After 4 days, mice were beginning to show symptoms of the illness. Mice which did not survive, one died, the remainder were euthanized-either as the result of having (a) lost 20% body-weight or (b) lost mobility due to apparent sickness.

The survival rate is shown in Table 2.

TABLE 2

| Day | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Group 1 | 100% | 100% | 100% | 100% | 90% | 40% | 20% | 20% | 20% | 20% | 20% | 20% | 20% | 20% | 20% | 20% |
| Group 2 | 100% | 100% | 100% | 100% | 10% | 10% | 0% | 0% | 0% | 0% | 0% | 0% | 0% | 0% | 0% | 0% |

Figure 3:
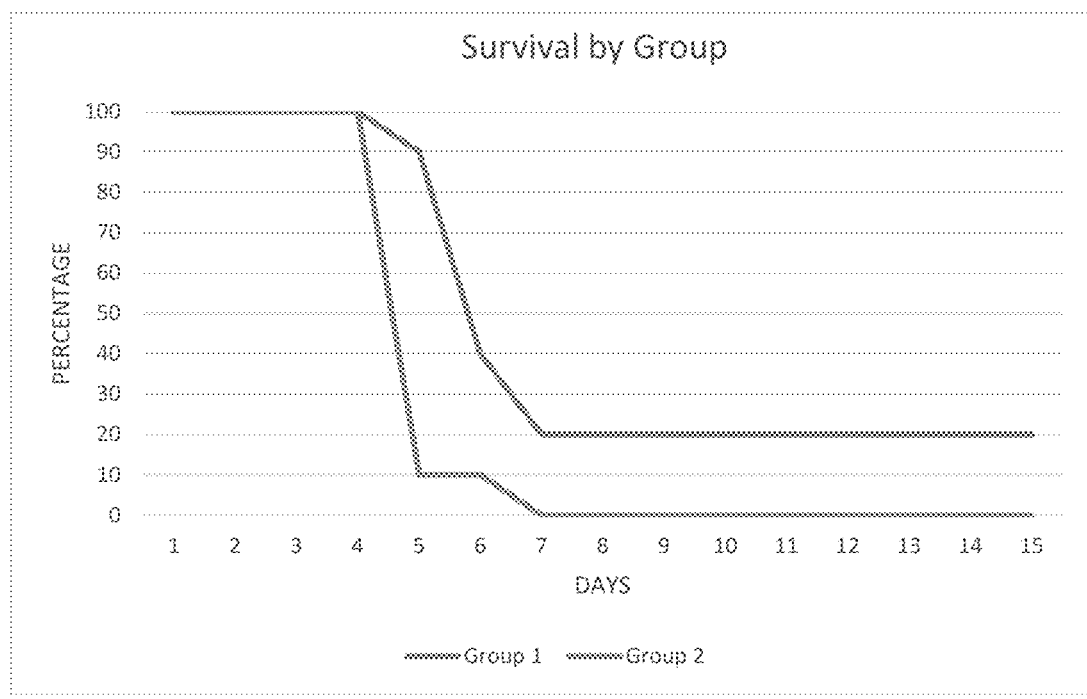
FIG. 3 is a graph showing the percent survival of mice infected with virus in two groups: Group 1 treated with a copolymer of the invention and Group 2 an infected control in accordance with Example 4.

The results are presented in the graph shown in FIG. 3.

The invention claimed is:

1. A method of treatment of a parenteral viral infection in a subject comprising systemically administering to the subject a copolymer comprising an acrolein-derived segment and a polyalkylene glycol oligomer segment, the copolymer having a molecular weight of no more than 1000 Daltons, wherein the copolymer is administered by a route selected from the group consisting of: oral administration, inhalation, transdermal delivery, injection and infusion.

2. The method according to claim 1, wherein the acrolein-derived segment is a polyacrolein oligomer comprising two or more acrolein residues.

3. The method according to claim 1, wherein the copolymer has a molecular weight of from 300 to 1000 Daltons.

4. The method according to claim 1, wherein the polyalkylene glycol oligomer segment has a molecular weight in the range of from 200 to 600 Daltons.

5. The method according to claim 1, wherein the polyalkylene glycol oligomer segment has a molecular weight in the range of from 200 to 400 Daltons.

6. The method according to claim 1, wherein a polyalkylene glycol of the polyalkylene glycol oligomer segment is polyethylene glycol.

7. The method according to claim 1, wherein the copolymer is administered by oral administration.

8. The method according to claim 1, wherein the copolymer is administered by intravenous injection or infusion.

9. The method according to claim 1, wherein the copolymer is administered as an aqueous solution comprising a copolymer concentration in the range of from 0.01% by weight to 20% by weight of the aqueous solution.

10. The method according to claim 1, wherein the copolymer is administered orally in the form of a tablet, caplet, syrup or liquid.

11. The method according to claim 1, wherein the copolymer is administered systemically at a dose in the range of from 1 mg to 1000 mg per kilogram of bodyweight per day.

12. The method according to claim 1, wherein the parenteral viral infection is selected from the group consisting of a influenza viral infection, an HIV infection, a hepatitis viral infection, a Ross River viral infection, and a herpes viral infection.

13. The method according to claim 1, wherein the parenteral viral infection is an influenza viral infection.

* * * * *